United States Patent [19]

Cox

[11] Patent Number: 4,464,358

[45] Date of Patent: Aug. 7, 1984

[54] HOMOCYCLIC DERIVATIVES

[75] Inventor: Michael T. Cox, Congleton, England

[73] Assignee: Imperial Chemical Industries PLC, London, England

[21] Appl. No.: 412,905

[22] Filed: Aug. 30, 1982

[30] Foreign Application Priority Data

Sep. 15, 1980 [GB] United Kingdom ................. 8127869

[51] Int. Cl.$^3$ .................... A61K 37/00; C07C 103/52; C07C 121/50; C07C 101/44; A01N 43/02; A01N 37/10

[52] U.S. Cl. .............................. 424/177; 260/112.5 R; 260/465 D; 260/465 E; 562/457; 560/48; 424/308; 424/278; 549/494

[58] Field of Search .................... 260/112.5 R, 465 D, 260/465 E; 424/177, 308, 278; 562/457; 560/48

[56] References Cited

PUBLICATIONS

S. N. Rastogi, et al., Indian Journal of Chemistry, vol. 9, (1971) 1175-1182.

Primary Examiner—Delbert R. Phillips
Attorney, Agent, or Firm—Cushman, Darby & Cushman

[57] ABSTRACT

Compounds of the formula:

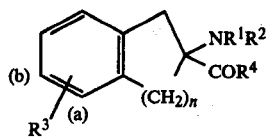

wherein $R^1$ stands for hydrogen or a defined hydrocarbyl or halogenoalkenyl radical, $R^2$ stands for a defined hydrocarbyl, halogenoalkenyl or furylmethyl radical, $R^3$ is a substituent at position (a) or (b) and stands for a hydroxy or defined alkoxy or alkanoyloxy radical, $R^4$ stands for a defined alkoxy, cyanoalkoxy or alkenyloxy radical or a defined amino acid residue or peptide residue, and n stands for 1, 2 or 3, and pharmaceutically-acceptable salts thereof. Processes for the manufacture of the compounds. Pharmaceutical compositions comprising one of the compounds and a pharmaceutical diluent or carrier. The compounds are antagonists at the opiate receptors, and most of them are selective δ-receptor antagonists.

5 Claims, No Drawings

HOMOCYCLIC DERIVATIVES

This invention relates to homocyclic derivatives and more particularly it relates to tetralin derivatives and related compounds which are active as antagonists at the opiate receptor in warm-blooded animals.

Shelver and Burger, J. Pharm. Sci., 1963, 52, 250, have described the synthesis of various tetralin derivatives as potential analgesic agents. The following compounds were described, amongst others:

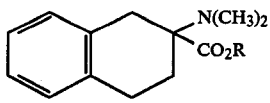   I in which R stands for a methyl or ethyl radical. The former compound, as well as others, was screened pharmacologically, but it did not exhibit analgesic properties in mice at doses up to 200 mg./kg., it gave no indication of central nervous system depression or excitation, and it did not produce hypoglycaemia three hours after oral administration of 100 mg./kg. to 18-hour fasted guinea pigs.

Shaw and Turnbull, European J. Pharmacol., 1978, 49, 313, have described various enkephalin analogues which are opiate receptor agonists, including the following compound:

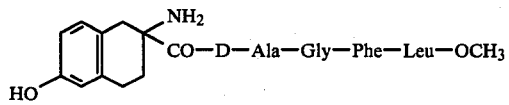   II (In this specification the standard abbreviations for amino acids are used, as discussed in more detail below).

Deeks, Crooks and Waigh, J. Pharm. Pharmacol., 1979, 31S, 62P, have described the synthesis and testing of the following enkephalin derivatives:

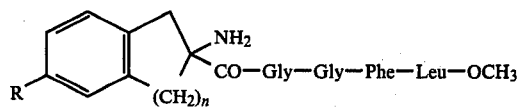   III in which R stands for hydrogen or a hydroxy radical, and n stands for 1 or 2. The compounds were found to be opiate receptor agonists having slightly greater opioid activity in the guinea pig ileum test than morphine or [Met]-enkephalin, but much lower activity than the latter compound in the mouse vas deferens test.

In United Kingdom patent specification No. 1,601,754 (published Nov. 4, 1981), and in the corresponding Belgian patent specification No. 867,121 (published Nov. 16, 1978), there are described inter alia the following compounds:

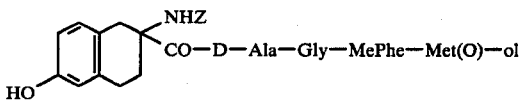   IV in which Z stands for hydrogen or a cyclobutylmethyl radical (see Table 2 in said specifications). The compounds are stated to exhibit analgesic activity, as indicated by their affinity for the opiate receptors in rat brains, as indicated by the method of Pert and Synder, Mol. Pharmacol., 1974, 10, 868, and by their activity in the tail flick test in mice. They also exhibit central nervous system activity, as indicated by their ability to inhibit spontaneous motor activity in mice, and they exhibit a stimulant effect on the secretion of growth hormone and prolactin as indicated in standard tests.

It is now generally recognised that in warm-blooded animals there are at least two distinct types of opiate receptor, i.e. the $\mu$-receptor and the $\delta$-receptor (see Robson and Kosterlitz, Proc. R. Soc. London (b), 1979, 205, 425, Goodman et al., Proc. Natl. Acad. Sci. U.S.A., 1980, 77, 6239, and Simon, Trends in Pharmacol. Sci., 1981, 2, 155). The compounds of the present invention are opiate receptor antagonists, in contrast to the opiate receptor agonists mentioned above. Moreover, most of the compounds of the invention are selective $\delta$-receptor antagonists, in contrast to the known opiate antagonists, for example naloxone, which are selective $\mu$-receptor antagonists.

According to the invention there are provided homocyclic derivatives of the formula:

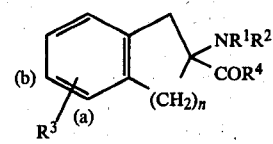   V wherein:

$R^1$ stands for hydrogen, an alkyl, alkenyl, halogenoalkenyl or alkynyl radical of not more than 6 carbon atoms, a cycloalkylmethyl radical in which the cycloalkyl radical contains not more than 6 carbon atoms, or a phenylalkyl radical in which the alkyl radical contains not more than 6 carbon atoms;

$R^2$, which may be the same as or different from $R^1$, stands for an alkyl, alkenyl, halogenoalkenyl or alkynyl radical of not more than 6 carbon atoms, a cycloalkylmethyl radical in which the cycloalkyl radical contains not more than 6 carbon atoms, or a furylmethyl radical; or $R^1$ and $R^2$ are joined to form, together with the adjacent nitrogen atom, a nitrogen-containing heterocyclic radical of 5 or 6 ring atoms;

$R^3$ is a substituent at ring position (a) or (b), and it stands for a hydroxy radical, an alkoxy radical of not more than 3 carbon atoms, or an alkanoyloxy radical of not more than 6 carbon atoms;

$R^4$ stands for an alkoxy, cyanoalkoxy or alkenyloxy radical of not more than 6 carbon atoms, or for an amino acid residue or peptide residue of the formula:

   VI containing one or more amino acid residues or $\alpha$-aza-amino-acid residues linked by conventional peptide linkages (—CO—NH—), and $R^5$ stands for a hydroxy radical, an alkoxy or alkenyloxy radical of not more than 6 carbon atoms, or an amino radical (—$NH_2$);

n stands for 1, 2 or 3; and wherein, when $R^1$ stands for hydrogen, n stands for 2, $R^2$ stands for an alkyl, alkenyl, halogenoalkenyl or alkynyl radical of not more than 4 carbon atoms, or a cyclopropylmethyl, cyclobutylmethyl or furylmethyl radical, $R^3$ stands for a hydroxy radical substituted on ring position (b), and $R^4$ stands for an alkoxy radical of not more than 4 carbon atoms; and pharmaceutically-acceptable salts thereof.

It will be appreciated by those skilled in the art that many of the compounds of the invention contain at least one assymmetric carbon atom. It is to be understood, therefore, that the compounds of this invention include not only the racemic forms thereof but also the optically-active forms which possess the properties described hereinafter. It is a matter of common general knowledge how to resolve a racemate into its optically-active isomers, and the opiate antagonist properties of said isomers can be determined by the tests referred to below.

$R^1$ may, for example, stand for hydrogen, or an alkyl, alkenyl, chloroalkenyl or alkynyl radical of not more than 4 carbon atoms, for example an n-propyl, allyl, 2-chloroallyl or propargyl radical, or a cyclopropylmethyl or cyclobutylmethyl radical, or a phenylalkyl radical in which the alkyl radical contains not more than 3 carbon atoms, for example 2-phenylethyl radical.

$R^2$ may, for example, stand for an alkyl, alkenyl, chloroalkenyl or alkynyl radical of not more than 4 carbon atoms, for example an n-propyl, allyl, 2-chloroallyl or propargyl radical, or a cyclopropylmethyl, cyclobutylmethyl or 2-furylmethyl radical.

Alternatively, $R^1$ and $R^2$ may be joined to form, together with the adjacent nitrogen atom, a saturated nitrogen-containing heterocyclic radical of 5 or 6 ring atoms, for example a pyrrolidino or piperidino radical.

$R^3$ may, for example, stand for a hydroxy, methoxy, acetoxy, isobutyryloxy or pivaloyloxy radical.

$R^4$ may, for example, stand for an alkoxy, cyanoalkoxy or alkenyloxy radical of not more than 4 carbon atoms, for example a methoxy, ethoxy, cyanomethoxy or allyloxy radical. Alternatively, $R^4$ may stand for an amino acid residue or peptide group as aforesaid. It is to be understood that in this specification the abbreviations used for amino-acids are standard abbreviations used in the peptide art (see Pure and Applied Chemistry, 1974, 40, 317–331, and Neuropeptides, 1981, 1, 231–235). An α-aza-amino-acid is one in which the α-CH group of an amino acid has been replaced by a nitrogen atom. The abbreviation for an α-aza-amino-acid is derived from that for the corresponding amino acid by adding the prefix "Az". Thus, for example, Azala stands for α-aza-alanine, Azgly stands for α-aza-glycine, and so on. When the configuration of a particular amino acid (excluding glycine and the α-aza-amino-acids) is not designated, it is to be understood that that amino acid has the natural L configuration. $R^4$ may, for example, stand for an amino acid or peptide residue of the formula VI containing one to four amino acid residues or α-aza-amino-acid residues selected from Gly, Azgly, Phe, D-Phe, Leu, Met, D-Met, Ala, D-Ala, Azala, Arg, Pro, D-Pro, D-Ser and Sar, which are linked by peptide linkages. Specific values for $R^4$ are, for example:

—Phe—OMe

—Gly—Gly—Phe—Leu—OH

—Gly—Gly—Phe—Met—OH.

A preferred value for n is 2.

The compounds of the invention in which $R^1$ does not stand for hydrogen, i.e. the tertiary amino derivatives, are preferred over those in which $R^1$ does stand for hydrogen. Even more preferred compounds are those wherein $R^1$ stands for an alkyl or alkenyl radical of not more than 4 carbon atoms, for example an n-propyl or allyl radical, or a cyclopropylmethyl radical, and $R^2$ stands for an alkenyl radical of not more than 4 carbon atoms, for example an allyl radical, or a 2-furylmethyl radical.

Particularly preferred compounds of the invention are:

methyl 2-N,N-diallylamino-6-hydroxy-1,2,3,4-tetrahydronaphthalene-2-carboxylate (i.e. in the racemic form) and the (+)-isomer thereof;

methyl 2-(N-allyl-N-n-propyl)amino-6-hydroxy-1,2,3,4-tetrahydronaphthalene-2-carboxylate;

methyl 2-(N-2-furylmethyl-N-n-propyl)amino-6-hydroxy-1,2,3,4-tetrahydronaphthalene-2-carboxylate; and methyl 2-(N-allyl-N-cyclopropylmethyl)amino-6-hydroxy-1,2,3,4-tetrahydronaphthalene-2-carboxylate;

and pharmaceutically-acceptable salts thereof.

The salts of the invention may, in the case where the compound of the formula V is sufficiently basic, be pharmaceutically-acceptable acid-addition salts or, in the case where the said compound is sufficiently acidic, pharmaceutically-acceptable base-addition salts. The said acid-addition salts are derived from an inorganic or organic acid which affords a pharmaceutically-acceptable anion, for example hydrochloric, phosphoric, acetic, citric or trifluoroacetic acid. The said base-addition salts are derived from a base which affords a pharmaceutically-acceptable cation, for example ammonia, N-methyl-D-glucosamine or arginine.

According to a further feature of the invention there is provided a process for the manufacture of the compounds of the formula V, wherein $R^1$, $R^2$, $R^3$, $R^4$ and n have the meanings stated above except that $R^2$ does not stand for a furylmethyl radical, and pharmaceutically-acceptable salts thereof, which comprises reacting a compound of the formula $QNH_2$, wherein Q stands for a group of the formula:

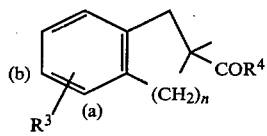

VII wherein $R^3$, $R^4$ and n have the meanings stated above, with a compound of the formula $R^6Z$, wherein $R^6$ stands for an alkyl, alkenyl, halogenoalkenyl or alkynyl radical of not more than 6 carbon atoms, a cycloalkylmethyl radical in which the cycloalkyl radical contains not more than 6 carbon atoms, or a phenylalkyl radical in which the alkyl radical contains not more than 6 carbon atoms, and Z stands for a halogen atom, in the presence of an acid-binding agent.

It will be appreciated by those skilled in the art that the above-mentioned process can be used to prepare N-monosubstituted and N,N-disubstituted derivatives, depending upon the conditions used, and in the N,N-disubstituted derivatives the $R^6$ substituents can be the same or different (in the latter case the monosubstituted derivative is prepared using one $R^6Z$ reactant, and the disubstituted derivative is obtained from that, using a $R^6Z$ reactant in which the $R^6$ radical is different). It is pointed out that in the case of the N-monosubstituted derivatives of the invention, i.e. where $R^1$ in the formula V stands for hydrogen, inter alia $R^2$ is restrictively defined (see the above definition of the compounds of the invention). It will be appreciated by those skilled in the art that this affects the definition of $R^6$, depending upon whether N-monosubstituted or N,N-disubstituted derivatives are to be produced by the above-mentioned process.

$R^6$ may, for example, stand for an n-propyl, allyl, 2-chloroallyl, propargyl, cyclopropylmethyl or 2-phenylethyl radical. Z may, for example stand for a chlorine or bromine atom. A suitable acid-binding agent is, for example, an alkali metal bicarbonate, for example sodium bicarbonate. The process is conveniently carried out in a suitable organic solvent, for example an alkanol of not more than 3 carbon atoms, for example methanol or ethanol, and it may be accelerated or completed by the application of heat, for example it may be carried out under reflux.

According to a further feature of the invention there is provided a process for the manufacture of compounds of the formula:

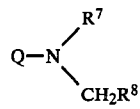

VIII wherein Q has the meaning stated above, $R^7$ stands for hydrogen or the group —$CH_2R^8$, wherein $R^8$ stands for an alkyl radical of not more than 5 carbon atoms, or a furyl or phenyl radical, or a phenylalkyl radical in which the alkyl radical contains not more than 5 carbon atoms, or $R^7$ and —$CH_2R^8$ are joined to form a tetramethylene or pentamethylene radical, and pharmaceutically-acceptable salts thereof, which comprises reacting a compound of the formula $QNH_2$, wherein Q has the meaning stated above, with an aldehyde of the formula $R^8CHO$ wherein $R^8$ has the meaning stated above, or with an α,ω-dialdehydoalkane in which the alkylene moiety is a dimethylene or trimethylene radical, under reducing conditions.

The aldehydo reactant may, for example, be propionaldehyde, 2-furaldehyde, phenylacetaldehyde or glutaraldehyde. The reducing conditions may, for example, be provided by a borohydride reducing agent, for example sodium borohydride or sodium cyanoborohydride, or by hydrogen in the presence of a hydrogenation catalyst, for example palladium on carbon. The process is conveniently carried out in a suitable organic solvent, for example an alkanol of not more than 3 carbon atoms, for example ethanol, optionally in the presence of acetic acid.

As in the case of the above-mentioned process involving a reactant of the formula $R^6Z$, the last-named process can be used to prepare N-monosubstituted and N,N-disubstituted derivatives, depending upon the conditions used. Also, in analogous fashion to that case, because $R^2$ in the formula V is restrictively defined when $R^1$ stands for hydrogen, the definition of $R^8$ depends upon whether an N-monosubstituted or N-N-disubstituted derivative is to be produced by the last-named process, i.e. the definition is narrower in the former case.

When the last-named process is used to prepare N,N-disubstituted derivatives, the —$CH_2R^8$ groups may be the same or different, i.e. in the latter case the two —$CH_2R^8$ groups are introduced into the molecule in a stepwise manner, in an analogous way to that outlined above in the case of the process involving the reactant of the formula $R^6Z$. Also, the two above-mentioned general processes themselves may be used in a stepwise manner to produce N,N-disubstituted derivatives. Therefore, according to a further feature of the invention there is provided a process for the manufacture of compounds of the formula:

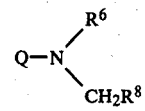

IX which comprises either:
(a) first preparing a compound of the formula:

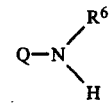

X by the above-mentioned general process involving the reactant of the formula $R^6Z$, and then reacting the product of the formula X with an aldehyde of the formula $R^8CHO$ under reducing conditions to produce the product of the formula IX; or (b) first preparing a compound of the formula:

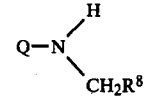

XI by the above-mentioned general process involving an aldehyde of the formula $R^8CHO$, and then reacting the product of the formula XI with a reactant of the formula $R^6Z$ as aforesaid to produce the product of the formula IX.

According to a further feature of the invention there is provided a process for the manufacture of the amino acid and peptide derivatives of the invention, and pharmaceutically-acceptable salts thereof, which comprises removing at least one peptide protecting group from a corresponding protected compound by conventional means.

The protected compound may, for example, be a t-butyl ester, i.e. $R^5$ (see formula VI) stands for a t-butoxy radical, and the protecting group may be removed by treating the protected compound with hydrogen chloride or trifluoroacetic acid. Hydrogen chloride may be used in the form of an aqueous solution, at a concentration between 1M and that of a saturated solution, or it may be used as a solution in an organic solvent, for example ethyl acetate, at a concentration in the range 2M to 6M. The process is preferably carried out at a temperature between 0° C. and ambient temperature, and optionally in the presence of a scavenger compound, for example anisole, thioanisole, methionine or dimethyl sulphide. Trifluoroacetic acid may be used as a de-protecting agent by itself, or it may be diluted with 5–10% by volume of water, and optionally an organic solvent, for example dichloromethane, may also be present. De-protection using trifluoroacetic acid may optionally be carried out in the presence of a scavenger compound, for example 2-mercaptoethanol or anisole.

According to a further feature of the invention there is provided a process for the manufacture of the compounds of the formula V wherein $R^1$, $R^2$, $R^3$ and n have the meanings stated above and $R^4$ stands for an alkoxy, cyanoalkoxy or alkenyloxy radical of not more than 6 carbon atoms, and pharmaceutically-acceptable salts thereof, which comprises esterifying the corresponding carboxylic acid.

The esterification is carried out by conventional methods, for example the carboxylic acid may be reacted with a compound of the formula $R^9Y$, wherein $R^9$ stands for an alkyl, cyanoalkyl or alkenyl radical of not more than 6 carbon atoms and Y stands for a chlorine, bromine or iodine atom, in the presence of an acid-binding agent, for example an alkali metal bicarbonate, for example sodium bicarbonate, or triethylamine or 1,5-diazabicyclo[5.4.0]undecene-5.

The esterification is conveniently carried out in a suitable solvent, and it may be accelerated or completed by the application of heat.

According to a further feature of the invention there is provided a process for the manufacture of the compounds of the formula V wherein $R^1$, $R^2$, $R^4$ and n have the meanings stated above, except that $R^1$ does not stand for hydrogen and $R^4$ does not stand for a group of the formula VI wherein $R^5$ stands for hydroxy, and wherein $R^3$ stands for an alkanoyloxy radical of not more than 6 carbon atoms, and pharmaceutically-acceptable salts thereof, which comprises alkanoylating the corresponding compound wherein $R^3$ stands for a hydroxy radical.

The alkanoylation may be carried out by reacting the hydroxy derivative with an alkanoyl halide of not more than 6 carbon atoms, for example acetyl chloride, isobutyryl chloride or pivaloyl chloride, in the presence of an acid-binding agent, for example triethylamine, or by reacting the hydroxy derivative with a corresponding acid anhydride.

The alkanoylation may conveniently be carried out in a suitable organic solvent for example dichloromethane.

According to a further feature of the invention there is provided a process for the manufacture of the compounds of the formula V wherein $R^1$, $R^2$ and n have the meanings stated above, $R^3$ stands for a hydroxy radical, and $R^4$ stands for an alkoxy radical of not more than 6 carbon atoms, and pharmaceutically-acceptable salts thereof, which comprises reacting the corresponding compound wherein $R^3$ stands for an alkoxy radical of not more than 3 carbon atoms, with strong aqueous hydrobromic acid at an elevated temperature.

In the last-named process $R^3$ may, for example, stand for a methoxy radical. The aqueous hydrobromic acid may, for example, have a concentration of approximately 48% w/v, and the process is conveniently carried out at a temperature in the range 100°–130° C., for example 120° C.

The starting materials used in the processes of the invention are either known compounds or they can be made by processes which are known for the preparation of chemically analogous compounds, as described in detail below.

The activity of the compounds of the invention as antagonists at opiate receptors has been demonstrated in the guinea pig ileum test ("ileum test") and the mouse vas deferens test ("vas test"); see the article by Shaw et al. in "Characteristics and Functions of Opioids", edited by Van Ree and Terenius, Elsevier/North-Holland Biomedical Press, 1978, 185–195. It is generally recognised that in the guinea pig ileum the $\mu$-type of opiate receptor predominates, and that in the mouse vas deferens the $\delta$-type of opiate receptor predominates. The potency of a compound in the above-mentioned tests is expressed as a Ke value, i.e. the concentration of the compound (antagonist) in the presence of which the agonist concentration has to be doubled in order to maintain a constant response. [Leu]-enkephalin is used as the agonist in both tests. The potency of any particular compound in the tests depends upon its precise chemical structure, but the compounds of the invention are active in the ileum test at a concentration in the range 1 nM to 30 $\mu$M, and in the vas test at a concentration in the range 1 nM to 10 $\mu$M ($\mu$M stands for micromolar, i.e. $10^{-6}$ mole per liter, and nM stands for nanomolar, i.e. $10^{-9}$ mole per liter.

As stated above, most of the compounds of the invention are selective $\delta$-receptor antagonists. It is to be understood that, using the above-mentioned tests, it is a relatively simple matter for one skilled in the art to establish the situation as regards selectivity in respect of any particular compound of the invention. Compounds of the invention which, in contrast to the majority, are more active at $\mu$-receptors than $\delta$-receptors are the compounds of Examples 19 and 21 below.

$LD_{50}$ data for a compound of the invention, namely methyl 2-N,N-diallylamino-6-hydroxy-1,2,3,4-tetrahydronaphthalene-2-carboxylate, which indicates its very low toxicity, is as follows:

(a) $LD_{50}$ in female mice: greater than 100 mg./kg. s.c.
(b) $LD_{50}$ in female mice: greater than 30 mg./kg. i.v.
(c) $LD_{50}$ in male rats: greater than 100 mg./kg. s.c.

Because of their activity as opiate receptor antagonists, the compounds of the invention may be used for the treatment of the following conditions and/or diseases in man: schizophrenia and other mental illnesses, stress, shock, stroke(cerebrovascular disorders), anorexia nervosa, epilepsy, disorders of the endocrine function including post-menopausal flushing, and gastro-intestinal disorders. The compounds may also be used as sedatives. When a compound of the invention is used for the treatment of man, it may be administered orally, or parenterally, for example by intravenous, subcutaneous or intramuscular injection or by infusion, or nasally, sub-lingually or rectally. A recommended daily oral dose for man is in the range 1 mg. to 1.0 g. Such a dose may be administered as a single daily dose or it may be divided into, for example, three doses per day. A recommended parenteral dose for man is 1 mg. to 250 mg., a recommended nasal dose is 0.1 mg. to 25 mg., a recommended sub-lingual dose is 1 mg. to 250 mg., and a recommended rectal dose is 2 mg. to 1.0 g.

The compounds of the invention may also be used as research tools or diagnostic agents in pharmacological or related studies.

According to a further feature of the invention there are provided pharmaceutical compositions comprising a compound of the formula V, wherein $R^1$, $R^2$, $R^3$, $R^4$ and n have the meanings stated above, or a pharmaceutically-acceptable salt thereof, and a pharmaceutically-acceptable diluent or carrier.

The pharmaceutical compositions of the invention may be in a form suitable for oral, parenteral, nasal, sub-lingual or rectal administration. Thus, for example, they may be in an orally-administrable unit dosage form, for example tablets or capsules, which may optionally be adapted for sustained or controlled release, or they may be in an injectable form, for example a sterile injectable solution or suspension, or in the form of a nasal spray or a suppository. All of the pharmaceutical compositions of the invention are obtainable in conventional manner using conventional diluents or carriers.

The pharmaceutical compositions of the invention may optionally contain, in addition to a homocyclic derivative of the invention:

(1) a known opiate antagonist, for example naloxone;

(2) a known psychotropic agent, for example an antipsychotic agent, for example chlorpromazine, or an antidepressant agent, for example imipramine, or an anxiolytic agent, for example chlordiazepoxide;

(3) a known analgesic agent, for example morphine; or (4) a known anticonvulsant agent, for example pyrimidone.

The invention is illustrated but not limited by the following Examples, in which the temperatures are expressed in degrees Celsius:

EXAMPLES 1 AND 2

Methyl 2-amino-6-hydroxy-1,2,3,4-tetrahydronaphthalene-2-carboxylate hydrochloride-hydrobromide (2 g.) was suspended in methanol (20 ml.) and neutralised by the addition of 7% w/v aqueous sodium bicarbonate solution (40 ml.) during 20 min. The resulting solution was extracted with chloroform (4×20 ml.) and the combined extracts were dried ($Na_2SO_4$) and the solvent evaporated in vacuo. Toluene (50 ml.) was added to the residue and evaporated in vacuo to remove residual traces of water. The resulting white solid was dissolved in ethanol (75 ml.), and to the solution were added sodium bicarbonate (3.3 g., 39 mM) and allyl bromide (3.4 ml., 39 mM). The mixture was stirred and refluxed for 5 hr. The solvent was evaporated in vacuo and the residue dissolved in a mixture of chloroform (50 ml.) and water (50 ml.). The mixture was separated, the organic phase dried ($Na_2SO_4$), and the solvent evaporated in vacuo. The residual mobile oil was chromatographed by the flash chromatography technique [J. Org. Chem., 43, 2923 (1978)] on a column of silica gel [Merck kieselgel 60 (70–230 mesh ASTM), hereinafter "kieselgel 60"; approx. 100 g.] using chloroform/methanol 98:2 v/v as eluant. The main faster-running component, having $R_f$ 0.35, was converted into the hydrochloride with saturated ethereal hydrogen chloride. The resulting white solid was crystallised from isopropanol to give methyl 2-N,N-diallylamino-6-hydroxy-1,2,3,4-tetrahydronaphthalene-2-carboxylate hydrochloride, m.p. 183°–5° (Example 1). The main slower-running component, having $R_f$ 0.19, was likewise converted into the hydrochloride, which was crystallised from 1:9 v/v aqueous isopropanol to give methyl 2-N-allylamino-6-hydroxy-1,2,3,4-tetrahydronaphthalene-2-carboxylate hydrochloride, m.p. 225°–8° (Example 2).

The methyl 2-amino-6-hydroxy-1,2,3,4-tetrahydronaphthalene-2-carboxylate hydrochloride-hydrobromide (i.e. a mixture of the two salts) used as starting material was obtained as follows:

2-Amino-6-hydroxy-1,2,3,4-tetrahydronaphthalene-2-carboxylic acid (15.5 g., 54 mM) was dissolved in methanol (150 ml.) and the solution was cooled to −20°. Thionyl chloride (6.9 ml.; 94 mM) was added dropwise during 30 min. and the reaction mixture was then stirred at room temperature for 6 days. The solvent was evaporated in vacuo, toluene (100 ml.) was added and then evaporated in vacuo. Ethyl acetate (150 ml.) was added to the resulting semi-solid, and the crystalline solid formed was collected by filtration. There was thus obtained methyl 2-amino-6-hydroxy-1,2,3,4-tetrahydronaphthalene-2-carboxylate as a mixture of the hydrochloride and hydrobromide salts of sufficient purity for use as described herein. The corresponding free base was obtained from the salt mixture by neutralisation with 7% w/v aqueous sodium bicarbonate solution in methanol and had $R_f$ 0.58 [thin layer chromatography (hereinafter "t.l.c.") on silica gel (kieselgel 60); elution with n-butanol/acetic acid/water 4:1:1 v/v].

EXAMPLES 3 TO 12

The procedure described in Examples 1 and 2, and in particular Example 1, was repeated using an equivalent amount of the appropriate starting materials (the halogeno reactant being the bromo compound, for example propargyl bromide, in each case), and there were thus obtained the following compounds (as the hydrochloride unless otherwise stated):

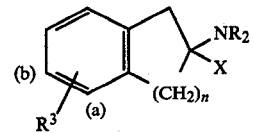

XII

| Example | n | R | $R^3$ [(b) unless otherwise stated] | X | Recrystallisation solvent | m.p. unless otherwise stated |
|---|---|---|---|---|---|---|
| 3 | 2 | allyl | OH | $CO_2Me$ | $Pr^iOH$ | 186–7° $[\alpha]_{578\,Hg}^{20}$ (MeOH) = +46.5° |
| 4 | 2 | allyl | OH | $CO_2Me$ | $Pr^iOH$ | 186–8° $[\alpha]_{578\,Hg}^{20}$ (MeOH) = −46.4° |
| 5* | 2 | propargyl | OH | $CO_2Me$ | toluene | 159–161° |
| 6 | 2 | cyclopropylmethyl | OH | $CO_2Me$ | ether (precipitation) | 192–3° |
| 7 | 2 | allyl | OH | $CO_2Et$ | $Pr^iOH$/ether | 175–7° |
| 8 | 2 | allyl | OH | —CO—Phe—OMe | — | $R_f$ 0.4 in 10:1 v/v $CH_2Cl_2$/MeOH |
| 9 | 2 | allyl | OMe(a) | $CO_2Me$ | EtOAc | 149–151° |
| 10 | 2 | allyl | OMe | $CO_2Me$ | ether (precipitation) | 149.5–151.5° |
| 11 | 1 | allyl | OH | $CO_2Me$ | $Pr^iOH$ | 174–5° |

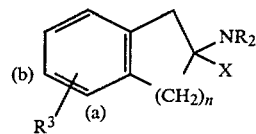

|         |   |       | R³<br>[(b) unless<br>otherwise |                   | Recrystallisation | m.p. unless<br>otherwise |
|---------|---|-------|--------------------------------|-------------------|-------------------|--------------------------|
| Example | n | R     | stated]                        | X                 | solvent           | stated                   |
| 12      | 3 | allyl |                                | OMe  CO₂Me        | EtOAc             | 144–6°                   |

*This compound was obtained as the free base.

EXAMPLES 13 TO 17

The procedure described in Examples 1 and 2, and in particular Example 2, was repeated using an equivalent amount of the appropriate starting materials (the halogeno reactant being the bromo compound except in the case of Example 14, where it was 2,3-dichloro-1-propene), and there were thus obtained the following compounds:

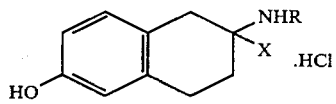

| Example | R           | X     | Recrystallisation<br>solvent | m.p. unless<br>otherwise<br>stated                |
|---------|-------------|-------|------------------------------|---------------------------------------------------|
| 13      | propargyl   | CO₂Me | Pr^iOH                       | 211–3°                                            |
| 14      | 2-chloroallyl | CO₂Me | EtOH/60–80°<br>petrol      | 205–7°                                            |
| 15      | allyl       | CO₂Me | EtOAc/MeOH/<br>60–80° petrol | 221–2.5°<br>$[\alpha]^{20}_{578\,Hg}$ (MeOH) = +27.7°<br>222–4° |
| 16      | allyl       | CO₂Me | EtOAc/MeOH/<br>60–80° petrol | $[\alpha]^{20}_{578\,Hg}$ (MeOH) = −27.1°         |
| 17      | allyl       | CO₂Et | ether<br>(precipitation)     | 216–8°                                            |

EXAMPLES 18 AND 19

Methyl 2-amino-6-hydroxy-1,2,3,4-tetrahydronaphthalene-2-carboxylate hydrochloride-hydrobromide (see Examples 1 and 2, 1 g.) was dissolved in ethanol (50 ml.) containing glacial acetic acid (0.39 ml., 6.6 mM). Sodium cyanoborohydride (0.41 g., 6.5 mM) and propionaldehyde (1.06 ml., 14.8 mM) were added, and the mixture was stirred at room temperature overnight. The solvent was evaporated in vacuo and the residue was shaken together with a mixture of ethyl acetate (20 ml.) and water (20 ml.). The mixture was separated and the organic phase was dried (Na₂SO₄). Saturated ethereal hydrogen chloride was added, the resulting mixture was filtered, and the solid residue was crystallised from ethanol to give methyl 6-hydroxy-2-N-n-propylamino-1,2,3,4-tetrahydronaphthalene-2-carboxylate hydrochloride, m.p. 235°–7° (Example 18).

The mother liquors from the crystallisation were evaporated in vacuo and the residue was dissolved in ethanol (20 ml.) containing acetic acid (0.13 ml., 2.2 mM). Propionaldehyde (0.36 ml., 5 mM) and sodium cyanoborohydride (0.14 g., 2.2 mM) were added, and the mixture was stirred at room temperature. After 5 hr. a further quantity of propionaldehyde (0.36 ml., 5 mM) was added and the mixture was stirred at room temperature overnight. The solvent was evaporated in vacuo and the residue was shaken together with a mixture of ethyl acetate (30 ml.) and saturated aqueous sodium bicarbonate solution (30 ml.). The mixture was separated, the organic phase was dried (Na₂SO₄) and the solvent evaporated in vacuo. The residue was purified by the flash chromatography technique on a column of silica gel (kieselgel 60, approx. 100 g.) using chloroform/methanol 97:3 v/v as eluant. Those fractions containing the required product, as located by t.l.c., were combined and the solvents evaporated in vacuo. Saturated ethereal hydrogen chloride was added to the residue, the resulting mixture was filtered, and the solid residue was crystallized from isopropanol to give methyl 6-hydroxy-2-N,N-di-n-propylamino-1,2,3,4-tetrahydronaphthalene-2-carboxylate hydrochloride, m.p. 206°–7° (Example 19).

EXAMPLE 20

Methyl 2-N-allylamino-6-hydroxy-1,2,3,4-tetrahydronaphthalene-2-carboxylate hydrochloride (see Example 2; 1.55 g., 5.9 mM) was dissolved in ethanol (50 ml.) containing glacial acetic acid (0.78 ml. 13.1 mM). Propionaldehyde (0.85 ml., 11.8 mM) and sodium cyanoborohydride (0.82 g., 13.1 mM) were added and the mixture was stirred at room temperature for 15 hr. More propionaldehyde (1.25 ml., 17.4 mM) was added and the mixture was stirred at room temperature overnight. The solvent was evaporated in vacuo and the residue was shaken together with a mixture of ethyl acetate (30 ml.) and saturated aqueous sodium bicarbonate solution (30 ml.). The mixture was separated, the organic phase was washed with saturated brine (20 ml.) and then dried (Na₂SO₄), and the solvent was evaporated in vacuo. The resulting gum was purified by the flash chromatography technique on a column of silica gel (kieselgel 60, approx. 100 g.) using chloroform/methanol 98:2 v/v as eluant. Those fractions containing the required product, as located by t.l.c., were concentrated in vacuo, and saturated ethereal hydrogen chloride was added to the residue. The resulting mixture was filtered, and the solid residue was crystallised from isopropanol to give methyl 2-(N-allyl-N-n-propyl)amino-6-hydroxy-1,2,3,4-tetrahydronaphthalene-2-carboxylate hydrochloride, m.p. 185°-8°.

EXAMPLE 21

Methyl 6-hydroxy-2-N-propargylamino-1,2,3,4-tetrahydronaphthalene-2-carboxylate hydrochloride (see Example 13, 0.24 g., 0.81 mM) was shaken together with a mixture of saturated aqueous sodium bicarbonate (20 ml.) and chloroform (20 ml.). The mixture was separated, the solvent in the organic phase was evaporated in vacuo, and the residue was dissolved in ethanol (20 ml.). Allyl bromide (0.35 ml., 4 mM) and sodium bicarbonate (0.34 g., 4 mM) were added, and the mixture was stirred and refluxed for 24 hr. The solvent was evaporated in vacuo and the residue was shaken together with a mixture of ethyl acetate (20 ml.) and saturated aqueous sodium bicarbonate solution (20 ml.). The mixture was separated and the solvent in the organic phase evaporated in vacuo. The residue was purified by the flash chromatography technique on a column of silica gel (kieselgel 60, approx. 100 g.) using chloroform/methanol 95:5 v/v as eluant. Those fractions containing the required product, as located by t.l.c., were combined and the solvents evaporated in vacuo to give methyl 2-(N-allyl-N-propargyl)-amino-6-hydroxy-1,2,3,4-tetrahydronaphthalene-2-carboxylate, m.p. 98°-102°.

EXAMPLE 22

The procedure described in Example 21 was repeated using the equivalent amount of the corresponding 2-chloroallylamino derivative (see Example 14) as starting material, and there was thus obtained methyl 2-[N-allyl-N-(2-chloroallyl)]amino-6-hydroxy-1,2,3,4-tetrahydronaphthalene-2-carboxylate as a gum having $R_f$ 0.29 (t.l.c. on kieselgel 60; methanol/dichloromethane 1:9 v/v).

EXAMPLE 23

The procedure described in Example 18 was repeated, but using the equivalent amount of 2-furaldehyde in place of the propionaldehyde, and there was thus obtained methyl 2-N-(2-furylmethyl)amino-6-hydroxy-1,2,3,4-tetrahydronaphthalene-2-carboxylate hydrochloride, m.p. 223°-4.5° (precipitated from ether).

EXAMPLE 24

The procedure described in Example 19 was repeated, but using the equivalent amount of glutaraldehyde in place of the propionaldehyde, and there was thus obtained methyl 6-hydroxy-2-piperidino-1,2,3,4-tetrahydronaphthalene-2-carboxylate hydrochloride, m.p. 228°-9° (precipitated from ether).

EXAMPLE 25

In analogous manner to that described in Example 20, methyl 2-(N-2-furylmethyl-N-n-propyl)amino-6-hydroxy-1,2,3,4-tetrahydronaphthalene-2-carboxylate hydrochloride, m.p. 129°-132°, precipitated from ether, was obtained from the corresponding N-2-furylmethylamino derivative and propionaldehyde.

EXAMPLE 26

In analogous manner to that described in Example 20, methyl 2-(N-allyl-N-2-phenylethyl)amino-6-hydroxy-1,2,3,4-tetrahydronaphthalene-2-carboxylate hydrochloride, m.p. 199°-201°, precipitated from ether, was obtained from the corresponding N-allylamino derivative (see Example 2) and phenylacetaldehyde.

EXAMPLE 27

The procedure described in Examples 1 and 2, and in particular Example 2, was repeated, but using an equivalent amount of cyclopropylmethyl bromide in place of the allyl bromide, and there was thus obtained methyl 2-N-cyclopropylmethylamino-6-hydroxy-1,2,3,4-tetrahydronaphthalene-2-carboxylate hydrochloride, m.p. 223°-4°, precipitated from ether.

EXAMPLE 28

A solution of 2-N,N-diallylamino-6-hydroxy-1,2,3,4-tetrahydronaphthalene-2-carboxy-Gly-Gly-Phe-Leu-OBu$^t$ (23 mg.) in dichloromethane (2 ml.) was stirred and cooled in a cold water bath. Trifluoroacetic acid-water 9:1 v/v (3 ml.) was added. The water bath was removed after 10 min. and stirring was then continued for 3 hr. The solvent was evaporated in vacuo, and toluene (10 ml.) was added and evaporated in vacuo. The residue was triturated with ether (10 ml.), and the resulting mixture was filtered to give 2-N,N-diallylamino-6-hydroxy-1,2,3,4-tetrahydronaphthalene-2-carboxy-Gly-Gly-Phe-Leu-OH trifluoroacetate, m.p. 95°-135°, $R_f$ 0.31 [Kieselgel 60, 5:1 v/v dichloromethane/methanol].

The tetrahydronaphthalene derivative used as starting material was obtained as follows:

Methyl 2-N,N-diallylamino-6-hydroxy-1,2,3,4-tetrahydronaphthalene-2-carboxylate (see Example 1, 2.4 g.) was dissolved in methanol (25 ml.) and the solution was degassed with argon. 10% v/v sodium hydroxide solution (12 ml.) was added to the stirred solution, and the mixture was heated for 24 hr. under reflux in an argon atmosphere. The mixture was cooled, 2N hydrochloric acid (15 ml.), was added and the mixture was filtered. The filtrate was evaporated in vacuo. Water (10 ml.) was added, the pH of the mixture was adjusted to pH 5.5 with an additional amount of 2N hydrochloric acid, and the mixture was evaporated in vacuo. Methanol (25 ml.) was added, and the mixture was evaporated in vacuo; this addition of methanol and subsequent evaporation was repeated once. The solid residue was triturated with methanol (30 ml.), the inorganic residue was collected by filtration, and the filtrate re-evaporated in vacuo to give the crude product as a solid. This solid was treated with boiling isopropanol (20 ml.), filtered hot to remove insoluble inorganic solid and then evaporated to give 2-N,N-diallylamino-6-hydroxy-1,2,3,4-tetrahydronaphthalene-2-carboxylic acid.

A mixture of the above-mentioned carboxylic acid (680 mg., 2.4 mM) and 1-hydroxybenztriazole (350 mg., 2.6 mM) in dry tetrahydrofuran (40 ml.) was stirred at room temperature. Dicyclohexylcarbodiimide (540 mg., 2.6 mM) was added, followed after 10 min. by H-Gly-Gly-Phe-Ley-OBu$^t$ (1.1 g., 2.45 mM). The mixture was stirred for 20 hr. Dilute acetic acid (2 ml.) was added, and the mixture was stirred for 30 min. Dicyclohexylurea was collected by filtration and washed with ether. The filtrate was evaporated in vacuo and the residue dissolved in acetone (10 ml.). After standing for 1½ hr. below 0°, the mixture was filtered and the filtrate evaporated in vacuo. The resulting foam was dissolved in ethyl acetate (50 ml.) and washed successively with saturated sodium bicarbonate solution (20 ml.), water (2×20 ml.), and saturated brine (20 ml.). The solution was dried ($Na_2SO_4$) and evaporated in vacuo, and the residue was chromatographed on kieselgel 60 (40 g.), eluting with ethyl acetate to give 2-N,N-diallylamino-6-hydroxy-1,2,3,4-tetrahydronaphthalene-2-carboxy-Gly-Gly-Phe-Leu-OBu$^t$, m.p. 95°–110°, R$_f$0.36 [kieselgel 60, ethyl acetate].

EXAMPLE 29

Allyl bromide (1.72 ml., 19.9 mM) was added to a stirred suspension of 2-amino-6-hydroxy-1,2,3,4-tetrahydronaphthalene-2-carboxylic acid hydrobromide (1.15 g., 4 mM.) and sodium bicarbonate (2.2 g., 26.2 mM) in 10% v/v aqueous methanol (40 ml.). The mixture was heated under reflux for 19 hr. After evaporation in vacuo, the residue was partitioned between ether (60 ml.) and water (30 ml.). The mixture was separated, both phases being retained, and the aqueous phase was extracted with ether (60 ml.). The combined organic phases were washed successively with water (3×30 ml.) and saturated brine (30 ml.). The solution was dried ($Na_2SO_4$) and evaporated in vacuo. The residual oil was chromatographed on kieselgel 60 (30 g., 70-230 mesh), starting the elution with dichloromethane, and increasing through 1% v/v methanol/dichloromethane to 2% v/v methanol/dichloromethane. The appropriate fractions were evaporated in vacuo, the residue was dissolved in ether (20 ml.), and ethereal hydrogen chloride was added until precipitation was complete. The mixture was evaporated in vacuo and triturated with ether. The mixture was filtered to give, as the solid residue, allyl 2-N,N-diallylamino-6-hydroxy-1,2,3,4-tetrahydronaphthalene-2-carboxylate hydrochloride, m.p. 160°–2°.

EXAMPLE 30

A suspension of 2-N,N-diallylamino-6-hydroxy-1,2,3,4-tetrahydronaphthalene-2-carboxylic acid hydrobromide (see Example 28; 210 mg., 0.6 mM) in dry acetonitrile (5 ml.) was stirred at room temperature under argon. Triethylamine (0.08 ml., 0.57 mM) was added, followed after 2 min. by DBU (1,5-diazabicyclo[5.4.0]-undecene-5; 0.09 ml., 0.6 mM), and 2 min. later by chloroacetonitrile (0.05 ml., 0.79 mM). The mixture was stirred for 1 hr., more DBU (0.08 ml., 0.53 mM) was added, and the mixture was stirred overnight (16 hr.). The solution was separated from insoluble gum and evaporated in vacuo (the residue being retained). The gum was partitioned between water (15 ml.) and ethyl acetate (20 ml.), and the organic phase was separated and added to the said residue. The organic solution was washed successively with saturated ammonium chloride solution (10 ml.) and saturated brine (15 ml.). The solution was dried ($Na_2SO_4$) and evaporated in vacuo. The residual oil was chromatographed on Kieselgel 60, eluting with 2:1 v/v ethyl acetate/petroleum ether (b.p. 60°–80°). The appropriate fractions were evaporated in vacuo, the residue was dissolved in ether (20 ml.), and ethereal hydrogen chloride was added until precipitation was complete. The mixture was filtered to give cyanomethyl 2-N,N-diallylamino-6-hydroxy-1,2,3,4-tetrahydronaphthalene-2-carboxylate hydrochloride, m.p. 85°–90°, R$_f$0.54 [kieselgel 60, 1:1 v/v ethyl acetate/petroleum ether (b.p. 60°–80°)].

EXAMPLE 31

Methyl 2-N,N-diallylamino-6-hydroxy-1,2,3,4-tetrahydronaphthalene-2-carboxylate hydrochloride (0.507 g., 1.5 mM.) was suspended in dry dichloromethane (10 ml.). To the stirred suspension, dry triethylamine (0.46 ml., 3.3 mM) was added, followed by acetyl chloride (0.129 ml., 1.8 mM). The mixture was stirred for 16 hr. at room temperature. The solvent was evaporated in vacuo and the residue dissolved in a mixture of ether (100 ml.) and water (100 ml.). The mixture was separated and the organic phase washed successively with water (2×70 ml.), dilute sodium bicarbonate (2×70 ml.), water (70 ml.), and saturated brine (70 ml.). The organic phase was dried ($Na_2SO_4$) and the solvent evaporated in vacuo. The oil-like product, in ethereal solution, was converted into the hydrochloride with saturated ethereal hydrogen chloride. There was thus obtained methyl 6-acetoxy-2-N,N-diallylamino-1,2,3,4-tetrahydronaphthalene-2-carboxylate hydrochloride, m.p. 144°–6°.

EXAMPLE 32

The product of Example 9 (1.0 g., 2.8 mM) was stirred in 48% w/v aqueous hydrobromic acid (10 ml.) at 120° for 70 min. The solution was cooled, and the precipitate filtered off and washed with ethanol (2×10 ml.). The solid was crystallized from water to give methyl 2-N,N-diallylamino-5-hydroxy-1,2,3,4-tetrahydronaphthalene-2-carboxylate hydrobromide, m.p. above 250°.

EXAMPLE 33

The product of Example 12 (1.0 g., 2.7 mM) was stirred in 48% w/v aqueous hydrobromic acid (10 ml.) at 120° for 45 min. The solution was cooled and evaporated in vacuo. The residue was partitioned between 7% w/v aqueous sodium bicarbonate solution (20 ml.) and chloroform (25 ml.). The mixture was separated, both phases being retained, and the aqueous phase was extracted with chloroform (25 ml.). The combined organic phase and chloroform extract was dried ($Na_2SO_4$) and evaporated in vacuo. The oily residue, in solution in ether, was converted into the hydrochloride salt with ethereal hydrogen chloride, and the hydrochloride was crystallised from ethanol/ethyl acetate. There was thus obtained methyl 6-N,N-diallylamino-2-hydroxy-5,6,7,8-tetrahydro-1H-benzocycloheptane-6-carboxylate hydrochloride, m.p. 176°–8°.

EXAMPLE 34

The procedure described in Example 31 was repeated, but using an equivalent amount of pivaloyl chloride in place of the acetyl chloride, and there was thus obtained methyl 2-N,N-diallylamino-6-pivaloyloxy-1,2,3,4-tetrahydronaphthalene-2-carboxylate hydrochloride, m.p. 164°–6° (precipitated from ether).

EXAMPLE 35

The procedure described in Example 31 was repeated, but using an equivalent amount of isobutyryl chloride in place of the acetyl chloride, and there was thus obtained methyl 2-N,N-diallylamino-6-isobutyryloxy-1,2,3,4-tetrahydronaphthalene-2-carboxylate hydrochloride, m.p. 125°–7° (precipitated from ether).

EXAMPLE 36

In analogous manner to that described in Example 21, but using the compound of Example 27 as the starting material, there was thus obtained methyl 2-(N-allyl-N-cyclopropylmethyl)amino-6-hydroxy-1,2,3,4-tetrahydronaphthalene-2-carboxylate hydrochloride, m.p. 181°–3° (precipitated from ether).

PREPARATION OF STARTING MATERIALS

Some of the above Examples are followed by a description of the method of preparation of novel starting materials used in them, and there now follow descriptions of the method of preparation of other novel starting materials:

SM1

This section describes the preparation of the starting materials used in Examples 3, 4, 15 and 16.

Methyl 2-amino-6-methoxy-1,2,3,4-tetrahydronaphthalene-2-carboxylate hydrochloride (13.6 g., 50 mM) was suspended in dry dichloromethane (200 ml.). The suspension was stirred and cooled in ice, and dry triethylamine (16.8 ml., 120 mM) was added, followed by acetyl chloride (4.3 ml., 60 mM). The mixture was stirred at room temperature for 16 hr. The solvent was evaporated in vacuo and the residue was dissolved in a mixture of ethyl acetate (1 l.) and water (500 ml.). The mixture was separated and the organic phase was washed successively with water (500 ml.), 2N hydrochloric acid (2×500 ml.), water (500 ml.) and saturated brine (500 ml.). The organic phase was dried ($Na_2SO_4$) and the solvent evaporated in vacuo. The solid was crystallised from ethyl acetate/petroleum ether (b.p. 60°–80°) to give methyl 2-acetylamino-6-methoxy-1,2,3,4-tetrahydronaphthalene-2-carboxylate, m.p. 160°–1°.

Methyl 2-acetylamino-6-methoxy-1,2,3,4-tetrahydronaphthalene-2-carboxylate (11.0 g., 39.7 mM) was dissolved in methanol (158 ml.). The solution was added to stirred distilled water (632 ml.) maintained at 37°. The pH of the resulting suspension was adjusted to 8.0 using a constant pH device (a pH meter coupled to an automatic titrator). The suspension was stirred and an alkaline protease (250 mg.; Subtilisin Carlsberg, obtainable from Sigma Chemical Company, St. Louis, Mo. 63178, U.S. item No. P 5380) was added. The pH of the suspension was maintained at 8.0 with 1N sodium hydroxide using the constant pH device. The suspension was stirred for 22 hr. until 50% hydrolysis of the ester had occurred. The mixture was cooled to room temperature and then filtered, both the solid residue and the filtrate being retained. The solid residue was thoroughly washed with distilled water and then dried in vacuo at 80°, to give optical isomer A of methyl 2-acetylamino-6-methoxy-1,2,3,4-tetrahydronaphthalene-2-carboxylate, m.p. 153°–4°. The combined filtrate and washings were washed with ethyl acetate (3×800 ml.). The aqueous phase was then acidified to pH 2.0 with 2N hydrochloric acid. The resulting mixture was filtered and the solid residue was washed thoroughly with distilled water and dried in vacuo at 80° to give optical isomer B of 2-acetylamino-6-methoxy-1,2,3,4-tetrahydronaphthalene-2-carboxylic acid, m.p. 252.5°–4°.

Optical isomer A of methyl 2-acetylamino-6-methoxy-1,2,3,4-tetrahydronaphthalene-2-carboxylate (3.45 g., 12.5 mM) was added to 48% w/v aqueous hydrobromic acid (34 ml.). The mixture was stirred and refluxed for 4 hr. The mixture was cooled, whereupon the product crystallised. It was collected by filtration and washed with ethyl acetate. The solid was dried in vacuo at 60° to give optical isomer A of 2-amino-6-hydroxy-1,2,3,4-tetrahydronaphthalene-2-carboxylic acid hydrobromide.

The last-named compound (3.14 g., 10.9 mM) was dissolved in methanol (35 ml.). The solution was cooled to 0° in an ice bath, and thionyl chloride (1.4 ml., 1.9 mM) was added over 5 min., keeping the temperature at 15° or lower. The mixture was stirred for 7 days at room temperature and then refluxed for 4 hr. The solution was cooled and filtered, the filtrate evaporated in vacuo, and the solid residue triturated with ethyl acetate. The crystalline solid so formed was collected by filtration. There was thus obtained optical isomer A of methyl 2-amino-6-hydroxy-1,2,3,4-tetrahydronaphthalene-2-carboxylate hydrochloride. This was used as the starting material in Examples 3 and 15.

Optical isomer B of methyl 2-amino-6-hydroxy-1,2,3,4-tetrahydronaphthalene-2-carboxylate hydrochloride was obtained in an analogous manner from optical isomer B of 2-acetylamino-6-methoxy-1,2,3,4-tetrahydronaphthalene-2-carboxylate acid, and the former compound was used as the starting material in Examples 4 and 16.

SM2

This section describes the preparation of the starting material used in Examples 7 and 17.

2-Amino-6-hydroxy-1,2,3,4-tetrahydronaphthalene-2-carboxylic acid hydrobromide (580 mg., 2.0 mM) was suspended in dry ethanol (15 ml.). Concentrated sulphuric acid (0.05 ml.) was added and the mixture was stirred under reflux. After 24 hr. reflux, more sulphuric acid (0.05 ml.) was added and the reflux was continued for 48 hr. The mixture was evaporated in vacuo. Ether (15 ml.) and ethyl acetate (20 ml.) were added to the residue, followed by water (10 ml.). The mixture was basified with dilute sodium bicarbonate solution, and then separated. The organic phase was washed successively with water (15 ml.) and saturated brine (15 ml.). The solution was dried ($Na_2SO_4$) and evaporated in vacuo, giving ethyl 2-amino-6-hydroxy-1,2,3,4-tetrahydronapthalene-2-carboxylate, $R_f$ 0.54 [kieselgel 60, 5:1 v/v dichloromethane/methanol].

SM3

This section describes the preparation of the starting material used in Example 8.

2-Amino-6-hydroxy-1,2,3,4-tetrahydronaphthalene-2-carboxylic acid (6 g., 29 mM) was stirred in trifluoroacetic acid (30 ml., 390 mM) at room temperature for 15 min. The mixture was stirred and cooled in an ice-water bath, and trifluoroacetic anhydride (10 ml., 70 mM) was slowly added. The cooling bath was removed and stirring continued for 4 hr. at room temperature. The mixture was evaporated in vacuo to give a gum, which was triturated with petroleum ether (b.p. 60°–80°). The resulting solid was collected by filtration, washed with petroleum ether (b.p. 60°–80°) and dried to give 6-hydroxy-2-trifluoroacetylamino-1,2,3,4-tetrahydronaphthalene-2-carboxylic acid, m.p. 70°–95°, $R_f$ 0.29 (kieselgel 60, ethyl acetate).

To a stirred solution of the last-named compound (600 mg., 1.98 mM) in ethyl acetate (6 ml.) was added a solution of dicyclohexylcarbodiimide (420 mg., 2.04 mM) in ethyl acetate (4 ml.). The mixture was stirred at room temperature for 1½ hr., and the precipitated dicyclohexylurea was collected by filtation and washed with ethyl acetate (2 ml.). Ethyl acetate (3 ml.), (S)-phenylalanine methyl ester hydrochloride (430 mg., 2.0 mM), and triethylamine (0.28 ml., 2.0 mM) were added to the stirred filtrate, and stirring was continued overnight (16 hr.). Water (10 ml.), 2N hydrochloric acid (2 ml.) and ethyl acetate (20 ml.) were added to the mixture. The resulting mixture was thoroughly shaken and then separated. The organic phase was washed successively with water (2×15 ml.) and saturated brine (2×15 ml.). The solution was dried (Na$_2$SO$_4$) and evaporated in vacuo, to give a gum. Trituration with petroleum ether (b.p. 60°–80°) and reevaporation in vacuo gave a foam, which was 6-hydroxy-2-trifluoroacetylamino-1,2,3,4-tetrahydronaphthalene-2-carboxy-(S)-phenylalanine methyl ester, m.p. 55°–63°, R$_f$ 0.33 (kieselgel 60, 20:1 v/v dichloromethane/methanol).

Sodium borohydride (400 mg., 10.5 mM) was added in portions over 25 min. to a stirred solution of the last-named compound (820 mg., 1.77 mM) in methanol (15 ml.). After 2 hr. more sodium borohydride (300 mg., 7.9 mM) was added in portions, and the mixture was stirred overnight (16 hr.). The mixture was evaporated in vacuo. Water (15 ml.) was added to the residue, and the mixture was acidified with 2N hydrochloric acid to pH 7 and then extracted with ethyl acetate (2×40 ml.). The organic extracts were combined and washed successively with water (20 ml.) and brine (20 ml.). The solution was dried (Na$_2$SO$_4$) and evaporated in vacuo to give a foam. The product was purified by the flash chromatography technique on a column of kieselgel 60 (120 g.) eluting with 10:1 v/v dichloromethane/methanol. The resulting gum was dissolved in ethyl acetate, acidified with ethereal hydrogen chloride, and diluted with ether to give 2-amino-6-hydroxy-1,2,3,4-tetrahydronaphthalene-2-carboxy-(S)-phenylalanine methyl ester hydrochloride as a hygroscopic solid, R$_f$ 0.36 (kieselgel 60, 5:1 v/v dichloromethane/methanol).

SM4

This section describes the preparation of the starting material used in Example 9.

A solution of 5-methoxy-2-tetralone (8.6 g., 48.9 mM) in ethanol (90 ml.) was added to a suspension of ammonium carbonate (23.0 g., 146 mM) and potassium cyanide (4.8 g., 74 mM) in water (90 ml.), and the mixture was stirred at 60° for 6 hr. After cooling, the mixture was diluted with water (200 ml.), the resulting mixture was filtered, and the solid residue refluxed in ethanol (500 ml.) for 10 min. The mixture was cooled and filtered. The solid residue was added to a mixture of 1,2-propanediol (60 ml.) and 40% w/v sodium hydroxide solution (20 ml.) at 140°, and stirred at that temperature for 22 hr. After cooling and dilution with water (150 ml.), the mixture was filtered through Celite and the pH adjusted to pH 1 with concentrated hydrochloric acid. A further filtration through Celite was followed by adjustment to pH 6.5 with concentrated ammonium hydroxide solution. The product was collected by filtration and washed with cold water. After thorough drying on the filter, the solid was stirred in methanol (100 ml.) and cooled to 0°. Thionyl chloride (2.1 ml., 29 mM) was added dropwise during 10 min. and the solution was then stirred at room temperature for 7 days. The reaction mixture was evaporated in vacuo, and toluene (50 ml.) was added and evaporated in vacuo. This addition of toluene and subsequent evaporation was repeated once, leaving a solid residue of methyl 2-amino-5-methoxy-1,2,3,4-tetrahydronaphthalene-2-carboxylate hydrochloride which was used without further purification.

SM5

This section describes the preparation of the starting material used in Example 10.

2-Amino-6-methoxy-1,2,3,4-tetrahydronaphthalene-2-carboxylic acid (16.5 g., 73.3 mM) was suspended in methanol (160 ml.), and the suspension was cooled to −15°. Thionyl chloride (9.3 ml., 128 mM) was added dropwise over 10 min., keeping the temperature to a maximum of −5°, and the reaction mixture was then stirred at room temperature for 6 days. The reaction mixture was then refluxed for 5 hr. The solvent was evaporated in vacuo, the solid residue triturated with ethyl acetate, and the crystalline solid so formed was collected by filtration. There was thus obtained methyl 2-amino-6-methoxy-1,2,3,4-tetrahydronaphthalene-2-carboxylate hydrochloride, m.p. 200°–2°.

SM6

This section describes the preparation of the starting material used in Example 12.

6-Methoxy-1-tetralone (10.0 g., 57 mM) was mixed with freshly sublimed zinc iodide, and the mixture was suspended in sodium-dry ether (150 ml.) and cooled to 5°. The suspension was stirred, and trimethylsilyl cyanide (7.5 ml., 60 mM) was added dropwise during 5 min. The reaction mixture was stirred at room temperature for 1 hr., and then a further portion of trimethylsilyl cyanide (2.5 ml., 20 mM) was added. Lithium aluminium hydride (4.3 g., 113 mM) was added portionwise during 15 min., and the mixture was stirred at room temperature overnight. The complex was decomposed, with stirring, by the sequential addition of water (4.3 ml.), 15% w/v aqueous sodium hydroxide solution (4.3 ml.), and water (12.9 ml.), whilst cooling the reaction flask in an ice-water bath. The mixture was filtered; both the solid residue and the filtrate being retained. The solid residue was extracted with chloroform (2×100 ml.). The combined filtrate and extracts were evaporated in vacuo. The solid residue was crystallised from ethyl acetate to give 1-aminomethyl-1-hydroxy-5-methoxy-1,2,3,4-tetrahydronaphthalene, m.p. 129°–130°.

The last-named compound (7.0 g., 34 mM) was stirred in aqueous acetic acid (1:9 v/v, 70 ml.) at 6°, and a solution of sodium nitrite (3.6 g., 42 mM) in water (40 ml.) was added during 10 min. at such a rate that the temperature did not exceed 9°. The mixture was stirred overnight at room temperature, and then ethyl acetate (30 ml.) was added. The mixture was separated, and the organic phase was washed successively with 7% w/v aqueous sodium bicarbonate solution (2×50 ml.) and saturated brine (50 ml.), and then evaporated in vacuo. The resulting oil was stirred with 40% v/v aqueous sodium metabisulphite solution (200 ml.) and water (140 ml.). The resulting solid bisulphite addition complex was collected by filtration, dried on the filter, and washed with ether. The solid was added to 10% w/v aqueous sodium carbonate solution (100 ml.) and ether (100 ml.) and stirred until the solid had dissolved. The mixture was separated, and the organic phase was washed with saturated brine (50 ml.), dried (Na$_2$SO$_4$), and evaporated in vacuo to give 2-methoxy-5,6,7,8-tetrahydro-1H-benzocycloheptan-6-one as a mobile oil, $R_f$ 0.45 [kieselgel 60, 1:9 v/v ethyl acetate/toluene].

The last-named compound (6.0 g., 31.6 mM) was dissolved in ethanol (75 ml.), the solution was added to a mixture of ammonium carbonate (14.9 g., 95 mM) and potassium cyanide (3.1 g., 48 mM) in water (75 ml.), and the mixture was stirred at 60° for 8 hr. After cooling and the addition of water (150 ml.), the resulting solid precipitate was collected by filtration. The solid was stirred under reflux together with 1,2-propanediol (36 ml.) and 40% w/v sodium hydroxide solution (12 ml.) for 24 hr. The mixture was cooled and filtered through Celite, and the filtrate was acidified to pH 1.5 with concentrated hydrochloric acid. The mixture was filtered through Celite, and the pH of the filtrate was adjusted to 6.5 with concentrated ammonium hydroxide solution. The resulting solution was evaporated in vacuo, and ice-cold water (100 ml.) was added to the residue. The resulting mixture was filtered, the solid residue being 6-amino-2-methoxy-5,6,7,8-tetrahydro-1H-benzocycloheptane-6-carboxylic acid.

The last-named compound (4.6 g., 19.6 mM) was stirred in methanol (100 ml.) at 0°, and thionyl chloride (2.5 ml., 34 mM) was added dropwise during 10 min. The mixture was stirred at room temperature for 3 days, and then under reflux for 48 hr. The solvent was evaporated in vacuo, and the residue was purified by the dry column chromatography technique to give methyl 6-amino-2-methoxy-5,6,7,8-tetrahydro-1H-benzocycloheptane-6-carboxylate hydrochloride as a gum which slowly crystallised, $R_f$ 0.3 [kieselgel 60, 1:4 v/v methanol/dichloromethane].

SM7

This section describes the preparation of the starting material used in Example 11.

A stirred suspension of 2-amino-5-hydroxy-2,3-dihydroindene-2-carboxylic acid (750 mg.) in methanol (10 ml.) was cooled to between −5° and −10° (isopropanolsolid $CO_2$ cooling bath). Thionyl chloride (0.6 ml., 8.2 mM) was added dropwise to the stirred mixture. The resulting solution was allowed to warm slowly to room temperature, and then stirred for 4 days at room temperature. The solvent was evaporated in vacuo, methanol (20 ml.) was added and then evaporated in vacuo. The residue was triturated with ether, and the solid was collected by filtration. There was thus obtained methyl 2-amino-5-hydroxy-2,3-dihydroindene-2-carboxylate hydrochloride, m.p. 216°–8°.

What we claim is:
1. A homocyclic derivative of the formula:

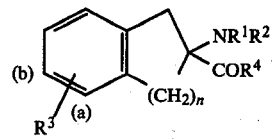

wherein:
R$^1$ stands for alkyl, alkenyl, chloroalkenyl or alkynyl, each of not more than 4 carbon atoms, or cyclopropylmethyl or cyclobutylmethyl;
R$^2$ stands for alkyl, alkenyl, chloroalkenyl or alkynyl, each of not more than 4 carbon atoms, or cyclopropylmethyl, cyclobutylmethyl or 2-furylmethyl;
R$^3$ is a substituent at ring position (a) or (b), and it stands for hydroxy, or methoxy or alkanoyloxy of not more than 5 carbon atoms;
R$^4$ stands for methoxy, ethoxy, cyanomethoxy, allyloxy, —Phe—OCH$_3$, —Gly—Gly—Phe—Leu—OH or Gly—Gly—Phe—Met—OH; and n stands for 2; or a pharmaceutically-acceptable salt thereof.

2. A compound as claimed in claim 1 wherein R$^1$ stands for alkyl or alkenyl of not more than 4 carbon atoms, or for cyclopropylmethyl and R$^2$ stands for alkenyl of not more than 4 carbon atoms, or for 2-furylmethyl.

3. A compound as claimed in claim 1 wherein R$^1$ stands for n-propyl, allyl, 2-chloroallyl, propargyl, cyclopropylmethyl or cyclobutylmethyl, R$^2$ stands for n-propyl, allyl, 2-chloroallyl, propargyl, cyclopropylmethyl, cyclobutylmethyl or 2-furylmethyl, R$^3$ is a substituent at position (a) or (b), and it stands for hydroxy, methoxy, acetoxy, butyryloxy or pivaloyloxy, and R$^4$ stands for methoxy, ethoxy, cyanomethoxy, allyloxy, —Phe—OCH$_3$, —Gly—Gly—Phe—Leu—OH or Gly—Gly—Phe—Met—OH.

4. A compound which is racemic or (+)-methyl 2-N,N-diallylamino-6-hydroxy-1,2,3,4-tetrahydronaphthalene-2-carboxylate, or methyl 2-(N-allyl-N-n-propyl)amino-6-hydroxy-1,2,3,4-tetrahydronaphthalene-2-carboxylate, methyl 2-(N-2-furylmethyl-N-n-propyl)amino-6-hydroxy-1,2,3,4-tetrahydronaphthalene-2-carboxylate, or methyl 2-(N-allyl-N-cyclopropylmethyl)amino-6-hydroxy-1,2,3,4-tetrahydronaphthalene-2-carboxylate, or a pharmaceutically-acceptable salt thereof.

5. A pharmaceutical composition suitable for use as an opiate receptor antagonist comprising a compound of the formula V, wherein R$^1$, R$^2$, R$^3$, R$^4$ and n have the meanings stated in claim 1, or a pharmaceutically-acceptable salt thereof, and a pharmaceutically-acceptable diluent or carrier.

* * * * *

UNITED STATES PATENT AND TRADEMARK OFFICE
CERTIFICATE OF CORRECTION

PATENT NO. : 4,464,358
DATED : August 7, 1984
INVENTOR(S) : Michael T. COX

It is certified that error appears in the above-identified patent and that said Letters Patent is hereby corrected as shown below:

Title page:

[30] change filing date of foreign application to:

--Sep. 15, 1981 [GB] ...-- rather than Sep. 15, 1980

Signed and Sealed this

Sixteenth Day of April 1985

[SEAL]

*Attest:*

DONALD J. QUIGG

*Attesting Officer*  *Acting Commissioner of Patents and Trademarks*